US00PP09418P

United States Patent [19]

Hesse

[11] Patent Number: Plant 9,418

[45] Date of Patent: Jan. 2, 1996

[54] CHRYSANTHEMUM PLANT NAMED 'CARIBBEAN ISLE'

[75] Inventor: Peter S. Hesse, Nipomo, Calif.

[73] Assignee: Clearwater Nursery, Inc., Nipomo, Calif.

[21] Appl. No.: 414,939

[22] Filed: Mar. 31, 1995

[51] Int. Cl.[6] ..... A01H 5/00

[52] U.S. Cl. ..... Plt./82.4

[58] Field of Search ..... Plt./74.1, 82.4

*Primary Examiner*—Howard J. Locker

*Attorney, Agent, or Firm*—Arnold, White & Durkee

[57] ABSTRACT

The present invention comprises a new and distinct cultivar of Chrysanthemum, botanically known as *Dendranthema grandiflora,* and referred to by the cultivar name Caribbean Isle.

1 Drawing Sheet

BACKGROUND OF THE NEW PLANT

Caribbean Isle originated from a cross made by Peter S. Hesse in a controlled breeding program at Clearwater Nursery, 887 Mesa Rd., Nipomo, Calif. 98444, USA.

The female parent of Caribbean Isle was the commercial variety Splendor (U.S. Plant Pat. No. 5,225) and the male parent was Hopscotch (U.S. Plant Pat. No. 5,816). Caribbean Isle was discovered and selected as one flowering plant within the progeny of the stated cross by Peter S. Hesse in November 1989, in a controlled environment in Nipomo, Calif.

The first act of asexual reproduction of Caribbean Isle was accomplished in January 1990, when vegetative cuttings were taken in a controlled environment at Clearwater Nursery, Nipomo, Calif., by Peter S. Hesse.

Horticultural examination of controlled flowerings of successive plantings has shown that the unique combination of characteristics as herein disclosed for Caribbean Isle are firmly fixed and are retained through successive generations of asexual reproduction.

Caribbean Isle has not been observed under all possible environmental conditions. The phenotype may vary significantly with variations in the environment such as temperature, light intensity and day length.

The following observations, measurements and comparisons describe plants grown in controlled environments at Clearwater Nursery, Nipomo, Calif. Unrooted cuttings were directly stuck into 6.5 inch pots and grown in a controlled environment under the natural temperature and day length prevailing in January 1990 to March 1990.

The following traits have been repeatedly observed and are determined to be basic characteristics of Caribbean Isle which, in combination, distinguish this Chrysanthemum as a new and distinct cultivar.

1. Flat Captiulum Form.
2. Daisy Capitulum Type.
3. Pink/Lavender fully expanded outer ray florets.
4. Yellow Daisy disc with green eye.
5. A diameter of 13.5 cm across the face of the capitulum.
6. Exceptional upright to spreading habit with an average of 4.0 breaks after a single pinch.
7. Flowering response is approximately 58 days from the start of short days.

8. Relatively easy to control plant height from bench such that the finished height will range from 40 to 45 centimeters depending on pot size and market requirements.

DESCRIPTION OF THE PHOTOGRAPH

The accompanying photograph shows typical infloresence and leaf characteristics of Caribbean Isle with the colors being as nearly true as possible with illustrations of this type. The photograph shows Caribbean Isle grown as a pinched spray pot mum with five (5 ) cuttings in a 6.5 inch pot.

DESCRIPTION OF THE PLANT

Of the commercial cultivars known to the inventor, the most similar in comparison to Caribbean Isle are the cultivars Splendor and Hopscotch. Reference is made to Table I which compares certain characteristics of Caribbean Isle to the same characteristics of the above mentioned cultivars. The botanical information set forth for each cultivar below was observed from the cultivars when grown in a side-by-side relationship under controlled conditions in Nipomo, Calif. All color references and designations set forth in Table I and throughout the specification are from The Royal Horticultural Society (R.H.S.) Colour Chart.

TABLE I

| CHARACTERISTIC | HOPSCOTCH | CARIBBEAN ISLE | SPLENDOR |
|---|---|---|---|
| CAPITULUM FORMS | Flat | Flat | Flat |
| CAPITULUM TYPE | Daisy | Daisy | Daisy |
| DIAMETER ACROSS FACE | 7.5 cm | 13.5 cm | 12.2 cm |
| BRANCHING PATTERN | Upright Spreading | Upright Spreading | Upright Spreading |
| BREAKS/PINCH | 4.4 | 4.0 | 4.0 |
| HEIGHT IN 6.5" POT WITH 1-2 APPLICATIONS B-NINE ™ | 40–45 cm | 40–45 cm | 40–45 cm |
| RESPONSE: TREATMENT | 8.5 weeks medium vigorous grower | 8.5 weeks medium vigorous grower | 9.0 weeks medium vigorous grower |
| DISC FLORETS | | | |
| DISC FLORET COLOR | Yellow | Yellow | Yellow |

TABLE I-continued

| CHARACTERISTIC | HOPSCOTCH | CARIBBEAN ISLE | SPLENDOR |
|---|---|---|---|
| NO. OF DISC FLORETS | 183.2 | 189.6 | 133.8 |
| LENGTH OF DISC FLORETS | 0.6 cm | 0.6 cm | 0.6 cm |
| RAY FLORETS | | | |
| COLOR | | | |
| FRONT: fully expanded | 9A Yellow | 65A and 11D Pink/Lavendar Yellow | 75A Purple |
| FRONT: unfolded ray florets | 9A Yellow | 65A and 11D Pink/Lavendar Yellow | 75A Purple |
| BACK: fully expanded outer ray floret | 6A Yellow | 65D Pink/Lavendar | 75D Purple |
| NUMBER | 32.6 | 52.0 | 52.3 |
| SHAPE | Elliptic | Elliptic | Elliptic |
| LENGTH | 3.85 cm | 6.0 cm | 5.2 cm |
| WIDTH | 1.43 cm | 1.8 cm | 1.5 cm |
| TOTAL NUMBER OF FLOWERS/ BREAK | 6.7 | 12.8 | 10.4 |
| LEAF | | | |
| COLOR: | Front: 147A Back: 147B | Front: 139A Back: 138A | Front: 139A Back: 138A |
| MATURE LEAF LENGTH: | Up to 10.2 cm | Up to 9.8 cm | Up to 8.4 cm |
| MATURE LEAF WIDTH: | 5.95 cm | 4.9 cm | 4.5 cm |

Similar traits of the three cultivars include the large flat, daisy capitulum. The diameter of the capitulum of Caribbean Isle tends to be larger than the capitulum of Splendor. Both Splendor and Caribbean Isle tend to have larger diameter capitulums than Hopscotch. All three cultivars have similar upright, spreading branching patterns and a similar number of breaks per pinch per plant. The finished plant height and the color of the disc florets is also similar for the three cultivars. Caribbean Isle and Hopscotch have similar numbers of disc florets. Both cultivars have more disc florets than Splendor. The length of the disc florets is similar for all three cultivars. The front ray floret color of Caribbean Isle is a blend of pink/lavendar 65A and yellow 11D, for Hopscotch yellow 9A, and for Splendor purple 75A. The back ray floret color of Caribbean Isle is pink/lavendar 65D, for Hopscotch yellow 6A, and for Splendor is purple 75D. Splendor and Caribbean Isle have a similar number of ray florets, but more than Hopscotch. The ray florets of all three cultivars are elliptic. Caribbean Isle has ray florets that are longer than those of Splendor. Hopscotch has darker leaves than either of the other cultivars. Hopscotch has the longest mature leaf length followed by Caribbean Isle, with Splendor having the shortest leaf. The three cultivars have similar leaf width. The response time from the start of short days is the same for Hopscotch and Caribbean Isle at 8.5 weeks. Response time is slightly higher for Splendor, 9.0 weeks.

THE PLANT

Classification:

*Botanical.*—*Dendranthema grandiflora.* Cultivar name: Caribbean Isle.

*Commercial.*—Flat daisy to be grown primarily as a Spray/CBR (center bud removed) or Disbud pot mum.

Inflorescence:

*Capitulum.*—Form: Flat. Type: Daisy. Diameter across face: average of 13.5 cm measured as a disbud.

*Ray florets.*—Color: Pink (general tonality within a distance of three (3) meters). Front: Fully expanded ray floret 65A & 11D. Front: Unfolded ray florets in center of flower 65A & 11D. Back: Fully expanded outer ray floret 65D. Shape: Elliptic.

*Corolla of disc florets.*—Color: Edge begins with 14A to Center Green 141C.

Reproductive organs:

*Androecium.*—Present in disc floret; pollen: scant.

*Gynoecium.*—Present in both ray and disc floret.

General appearance:

*Height.*—When grown in a 6.5 inch pot with 1–4 applications of B-NINE™ at the rate of 2500 ppm, the total plant height from the bottom of the pot may be maintained at 16–18 inches. Branching Pattern: Upright and spreading with an average of 4.0 breaks when grown with one pinch.

*Foliage.*—Color: (upper surface) 139A. Color: (lower surface) 138A. Shape: (see photograph).

What is claimed is:

1. A new and distinct Chrysanthemum plant named Caribbean Isle substantially as herein described and shown, characterized by its pink/lavendar floret coloration and excellent upright spreading habit.

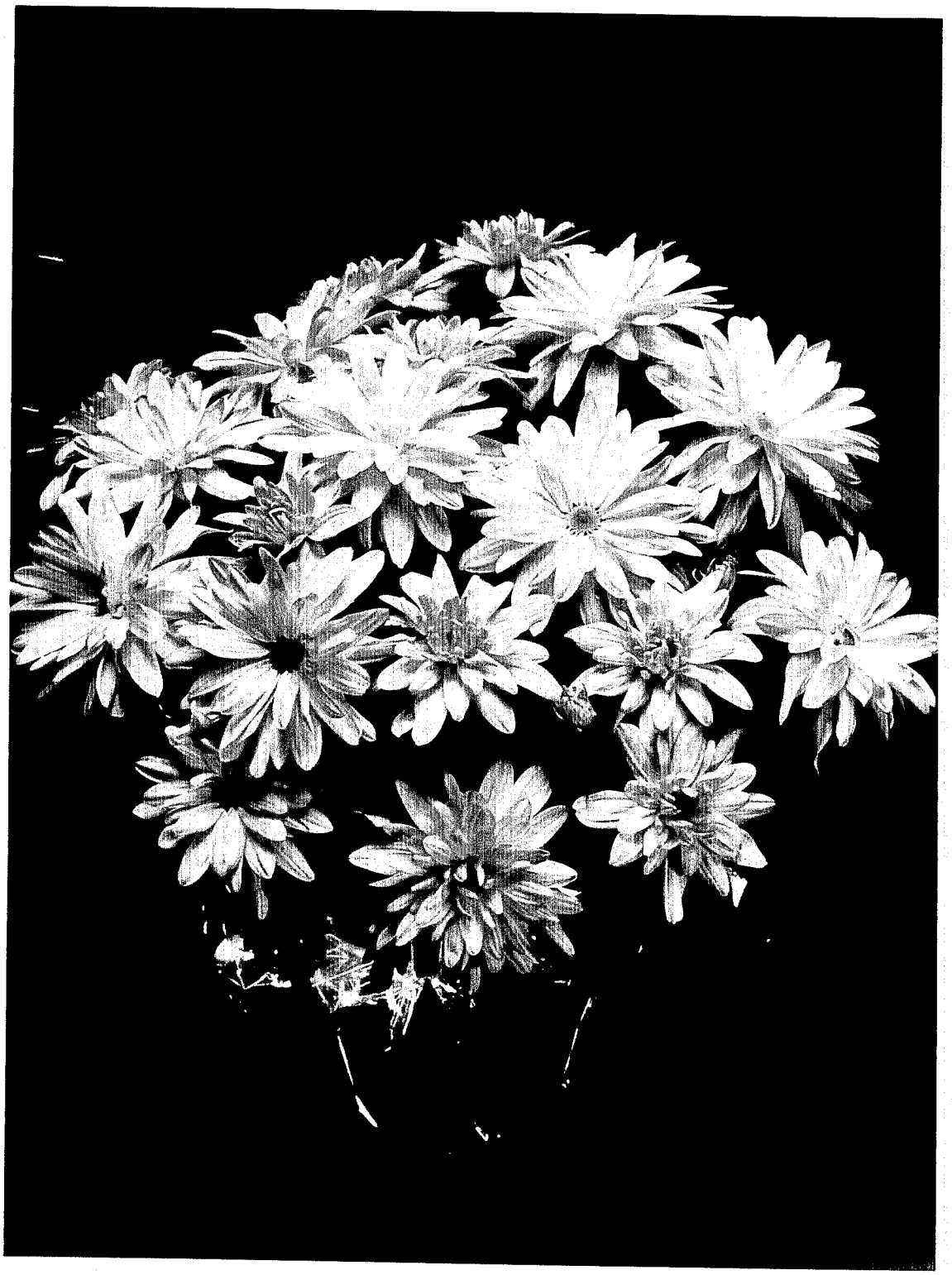

* * * * *